United States Patent [19]
Rosenschein et al.

[11] Patent Number: 5,984,882
[45] Date of Patent: Nov. 16, 1999

[54] METHODS FOR PREVENTION AND TREATMENT OF CANCER AND OTHER PROLIFERATIVE DISEASES WITH ULTRASONIC ENERGY

[75] Inventors: Uri Rosenschein, Kfar Daniel; Arie Rozenszajn, Ramat Hasharon, both of Israel

[73] Assignee: Angiosonics Inc., Morrisville, N.C.

[21] Appl. No.: 08/991,948

[22] Filed: Dec. 16, 1997

Related U.S. Application Data

[63] Continuation-in-part of application No. 08/858,247, May 19, 1997, which is a continuation-in-part of application No. 08/700,064, Aug. 19, 1996, Pat. No. 5,836,896.

[51] Int. Cl.$^6$ ...................................................... A61N 7/00
[52] U.S. Cl. ...................... 601/2; 600/2; 604/22
[58] Field of Search .............................. 601/2, 3; 604/22; 600/639, 1, 2

[56] References Cited

U.S. PATENT DOCUMENTS

| | | |
|---|---|---|
| 4,315,514 | 2/1982 | Drewes et al. |
| 5,571,523 | 11/1996 | Lee . |
| 5,836,896 | 11/1998 | Rosenschein . |

OTHER PUBLICATIONS

Miller, D.C., Circulation 70:153A, 1984.
Kerr, J.F.R. et al., 1994, Cancer 73:2013.
Williams, G.T., 1991, Cell 65:1097.
Fisher, D.E., 1994, Cell 78:539–542.
Steller, H. 1995, Science 267:1445–1449.
Attardi, L.D. et al., 1996, EMBO J 15:3693–3701.
Packham, G. et al., 1996, Oncogene 13:461–469.
Lane, D.P., 1992, Nature 358:15.
Yang, E., et al., 1995, Cell 80:285.
Wagner, A.J., 1994, Genes Dev. 8:2817–2830.
Walker, P.R., et al., 1994, Biochem. Cell Biol. 73:615–623.
Buttke, M.T. and Sandstrom, P.A., 1994, Immunol. Today 15:7–10.
Hockenbery, D.M., et al., 1993, Cell 75:241–251.
Chung, L.W., et al., 1992, J. Cell Biochem. Supplm. 16H:99–105.
Vermes, I., 1995, J. Immunol. Methods 184:34–51.
Fadok, V.A., 1992, J. Immunol. 143:2207.
McCloskey, T.W., et al., 1994, Clin. Immunol. Immunopathol. 71:14–18.

*Primary Examiner*—Ruth S. Smith
*Attorney, Agent, or Firm*—Stroock & Stroock & Lavan LLP

[57] ABSTRACT

A device and methods for inducing apoptosis in precancerous, cancerous and hyperproliferating cells by applying ultrasonic energy. The methods can include use of ultrasonic energy in combination with antioxidants and/or conventional therapies such as hormonal therapy, radiation therapy or chemotherapy. The device for the ultrasonic energy source can include a transmitter and a control unit.

24 Claims, 12 Drawing Sheets

PHA-activated human lymphocytes 72h after ULS treatment

PHA-activated human lymphocytes untreated (control)

Lymphocytes from Chronic Lymphatic Leukemia 48h after ULS treatment

Lymphocytes from Chronic Lymphatic Leukemia untreated (control)

Lymphocytes from Cronic Lymphatic Leukemia 8h after ULS treatment

Lymphocytes from Chronic Lymphatic untreated (control)

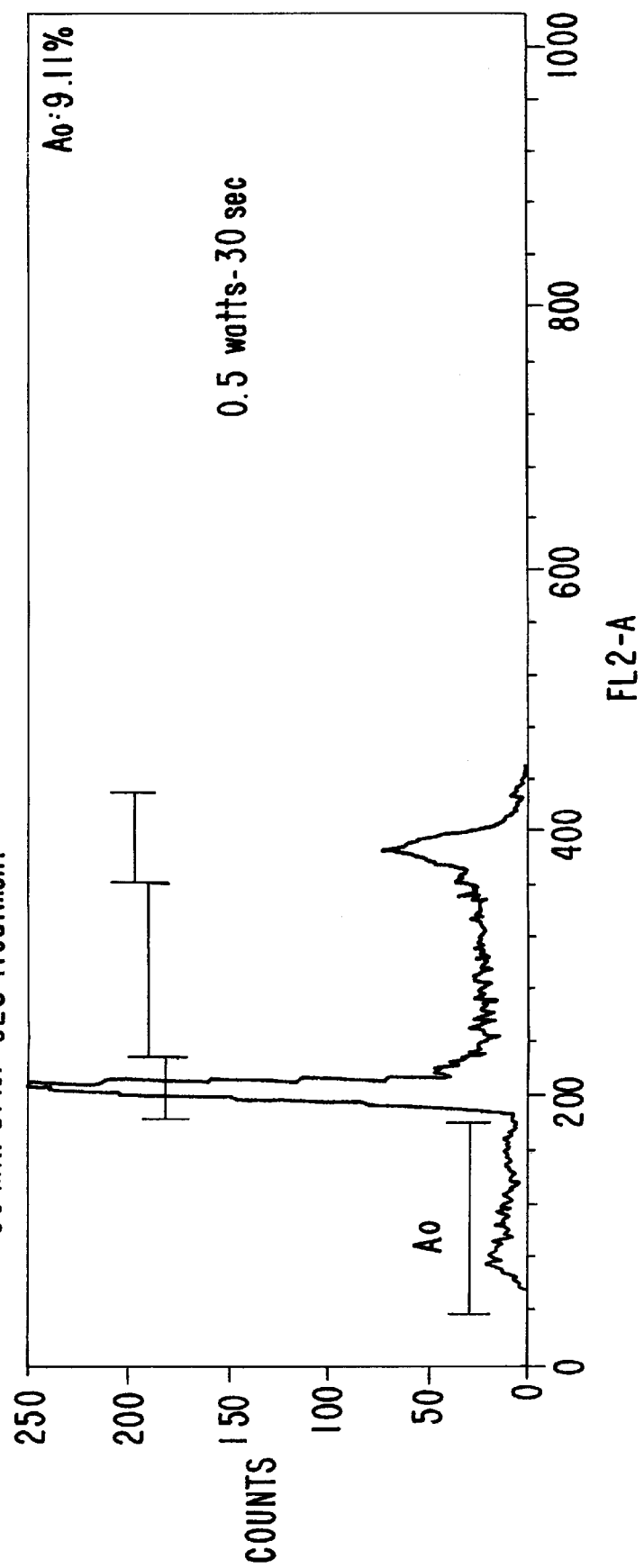

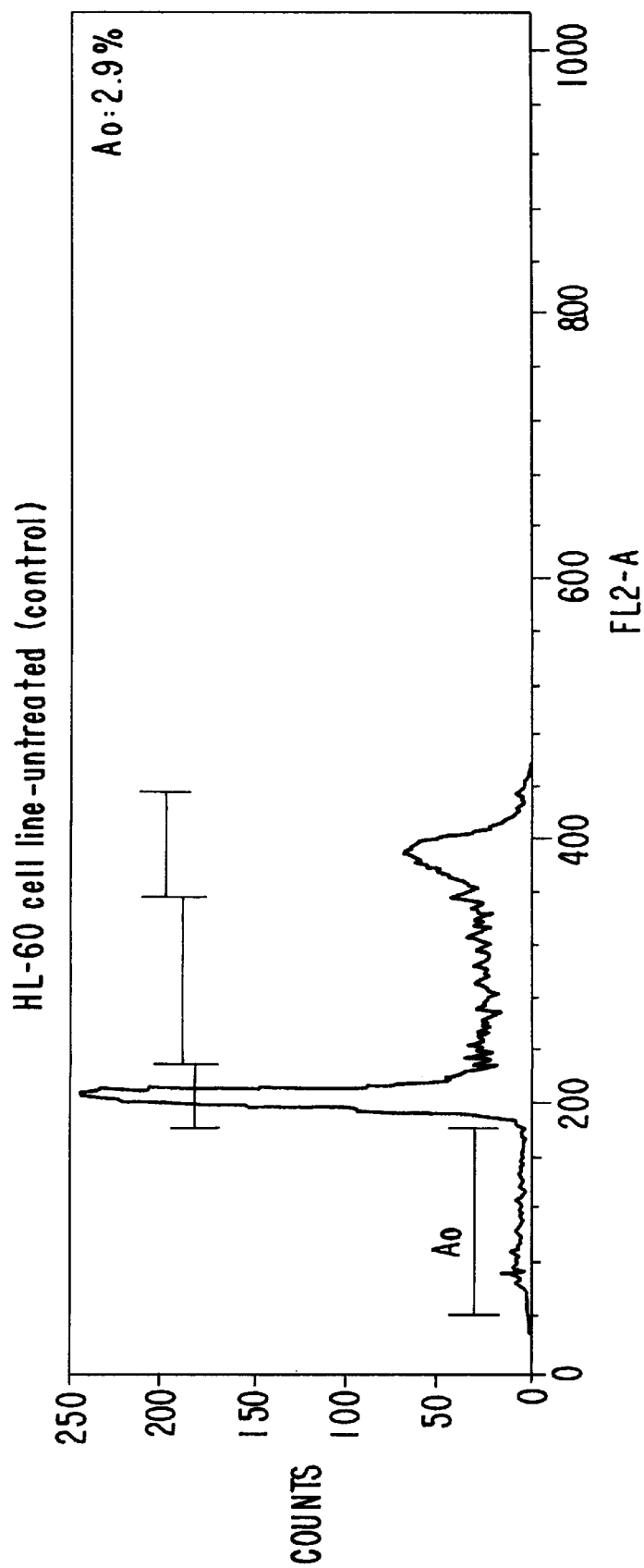

Apoptotic morphology of PHA-activated lymphocytes after ULS treatment

Apoptotic morphology of CLL lymphocytes after ULS treatment.

Apoptotic morphology of
CLL lymphocytes after ULS treatment.

METHODS FOR PREVENTION AND TREATMENT OF CANCER AND OTHER PROLIFERATIVE DISEASES WITH ULTRASONIC ENERGY

CROSS REFERENCE TO RELATED APPLICATIONS

This application is a continuation-in-part of U.S. application Ser. No. 08/858,247, filed on May 19, 1997, which is a continuation-in-part of U.S. application Ser. No. 08/700,064, filed on Aug. 19, 1996 which issued on Nov. 17, 1998 as U.S. Pat. No. 5,836,896. The contents of these applications are incorporated herein by reference.

BACKGROUND OF THE INVENTION

The invention relates generally to a device and method for preventing and treating diseases and more particularly to devices and methods for preventing and/or treating diseases with the application of ultrasound to targeted sites within a mammalian body. The present invention relates to devices and methods for preventing or treating cancers and other cell proliferative diseases such as arteriosclerosis, in mammals, by inducing or stimulating apoptosis within the target cells with ultrasonic energy. In particular, the devices and methods of the invention are useful in the stimulation of cell death and/or the inhibition of cell proliferation in cancer and other target cells. In the practice of the invention, ultrasonic energy can be further applied to antagonize the growth-factor-induced repression of apoptosis, to enhance the pro-apoptotic function of cytotoxic agents or hormonal or radiation therapy and/or to stimulate the pro-apoptotic actions of antioxidants.

Cancer is the second leading cause of death in the United States, accounting for approximately 450,000 deaths annually. Cancer is characterized primarily by an increase in the number of abnormal cells derived from a given normal tissue, invasion of adjacent tissues by these abnormal cells, and lymphatic or blood-borne spread of malignant cells to regional lymph nodes and to distant metastatic sites. Thus, insight into the complex events and strategies that lead from normal cellular growth and death to cancer, invasion and metastasis is important for the development of therapeutic strategies.

The complications of arteriosclerosis account for one half of all deaths in the United States and are the leading cause of permanent disability (Circulation 70:153A, 1984). A primary initiating factor in the formation of the atheromatous plaques is the proliferation of smooth muscle cells in the intima. Other conditions involving abnormal proliferation of target cells include vascular and fibrotic proliferative diseases, retinopathies, eczema or psoriasis. "Target cells" as used herein include, but are not limited to, precancerous cells, cancerous cells, cells having specific growth receptors and surrounding stromal cells in different tissues. The receptors for growth factors may include, but are not limited to, the epidermal growth factor (EGF), transforming growth factors (TGF alpha and beta), nerve growth factor (NGF), fibroblast growth factor (FGF), or insulin-like growth factors (IGF, I and II) or platelet-derived growth factor (PDGF).

Apoptosis is a mechanism by which cells are programmed to die under a wide range of physiological, biochemical and developmental stimuli. From the perspective of cancer, apoptosis is both a mechanism which suppresses tumorigenesis and is a predominant pathway in antineoplastic therapy. Many cancer cells circumvent the normal apoptotic mechanisms to prevent their self-destruction because of the many mutations they harbor. Thus, disarming apoptosis and other surveillance mechanisms is of fundamental significance in allowing the development of the malignant and metastatic phenotype of a cancer cell (Kerr, J. F. R. et al., 1994, Cancer 73:2013; and Williams, G. T., 1991, Cell 65:1097).

Apoptosis is also an important cellular response to a large variety of stress signals including, but not limited to, ionizing radiation, UV radiation, heat, growth factor deprivation, certain cytokines (like tumor necrosis factor (TNF) $\alpha$ and interferon (IFN) $\beta$), as well as many chemotherapeutic drugs (Fisher, D. E., 1994, Cell 78:539–542). However, none of the modalities currently employed to induce apoptosis involve the use of ultrasonic energy.

SUMMARY OF THE INVENTION

In accordance with the invention, a device and method are provided for the prevention and treatment of diseases by applying ultrasound therapy. The device can include a probe to be inserted into a site within the body or a transducer for focusing ultrasound at a site within the body in a noninvasive manner. The preventive and/or treatment method can involve inducing apoptosis or programmed cell death to thereby prevent and/or treat a variety of diseases or conditions and provide a variety of benefits.

The present invention can provide a method of preventing cancer by applying ultrasonic energy which induces apoptosis or programmed cell death of precancerous cells in different tissues and organs of a mammal. The method can include subjecting the precancerous cells to ultrasonic energy in an effective amount to trigger and induce programmed cell death in the precancerous cells.

The present invention can also provide a therapeutic method for the treatment of cancer, associated with programmed cell death or apoptosis of cancerous cells by exposing the cancer cells to ultrasonic energy in an amount effective to induces apoptosis of cancer cells.

In accordance with the invention, a system is also provided for the prevention and therapy of cancer following surgical removal of a primary cancerous lesion, which includes an ultrasonic energy source coupled to a transmitter which transmits the ultrasonic energy to the area of the excision of the primary lesion in an effective amount of ultrasonic energy for inducing apoptosis of remaining precancerous or cancerous cells.

According to an additional aspect of the present invention, there is provided a method to induce apoptosis of cancer cells by applying ultrasonic energy along with antioxidant therapy, including the administration of an effective amount of an antioxidant such as vitamin E, N-acetylcysteine, glutathione, vitamin C, cysteine, methionine, 2-mercaptoethanol and/or photosensitizing molecules.

According to yet another aspect of the present invention, there is provided a method to induce apoptosis of precancerous or cancerous cells including the application of ultrasonic energy in combination with a conventional therapeutic regimen including radiation therapy, hormonal therapy or one or more cytotoxic agents.

According to an additional aspect of the present invention, there is provided a device and method for inducing apoptosis of growth factor receptor-bearing cancer cells, supporting stromal cells and associated metastatic cells, by transmitting to the cells an effective amount of ultrasonic energy to induce apoptosis.

The present invention also provides devices and methods for inducing apoptosis of cells undergoing abnormal proliferation, for example, in conditions including arteriosclerosis, vascular and fibrotic proliferative diseases, retinopathies, eczema or psoriasis, by applying ultrasonic energy alone or in combination with an effective amount of one or more antioxidants including vitamin E, N-acetylcysteine, reduced glutathione, vitamin, C, cysteine, methionine, 2-mercaptoethanol or photosensitizing molecules.

In accordance with the invention, a system for the induction of apoptosis in precancerous, cancerous and other target cells is also provided, which includes an ultrasonic energy source coupled to a transmitter which transmits the ultrasonic energy to the cells, and a control unit which controls the amount of ultrasonic energy transmitted to the blood vessel to an effective amount for launching the apoptotic machinery of the cell.

The present invention is based on the unexpected discovery that ultrasonic energy is effective in inducing apoptosis.

It is the object of the present invention to provide a method for inducing apoptosis in aging cells and/or tissues that show functional deficit and to trigger renewal of cells and tissues.

It is also the object of the present invention to provide a method for inducing apoptosis in precancerous and cancerous cells.

It is another object of the present invention to provide a therapeutic method for preventing recurrence of a tumor after surgical removal of the primary cancerous lesion.

It is also an object of the present invention to provide a method for inducing apoptosis in target cells having one or more growth factors including, but not limited to EGF, TGF, NGF, FGF, IGF, PDGF.

It is also an object of the present invention to provide a method for inducing apoptosis in cells undergoing abnormal proliferation using ultrasonic energy alone or in combination with an effective amount of one or more antioxidants.

Still other objects and advantages of the invention will in part be obvious and will in part be apparent from the specification.

The invention accordingly comprises the several steps and the relation of one or more of such steps with respect to each of the others, and the apparatus embodying features of construction, combinations of elements and arrangement of parts which are adapted to effect such steps, all as exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DETAILED DESCRIPTION OF THE INVENTION

Figure 1A:
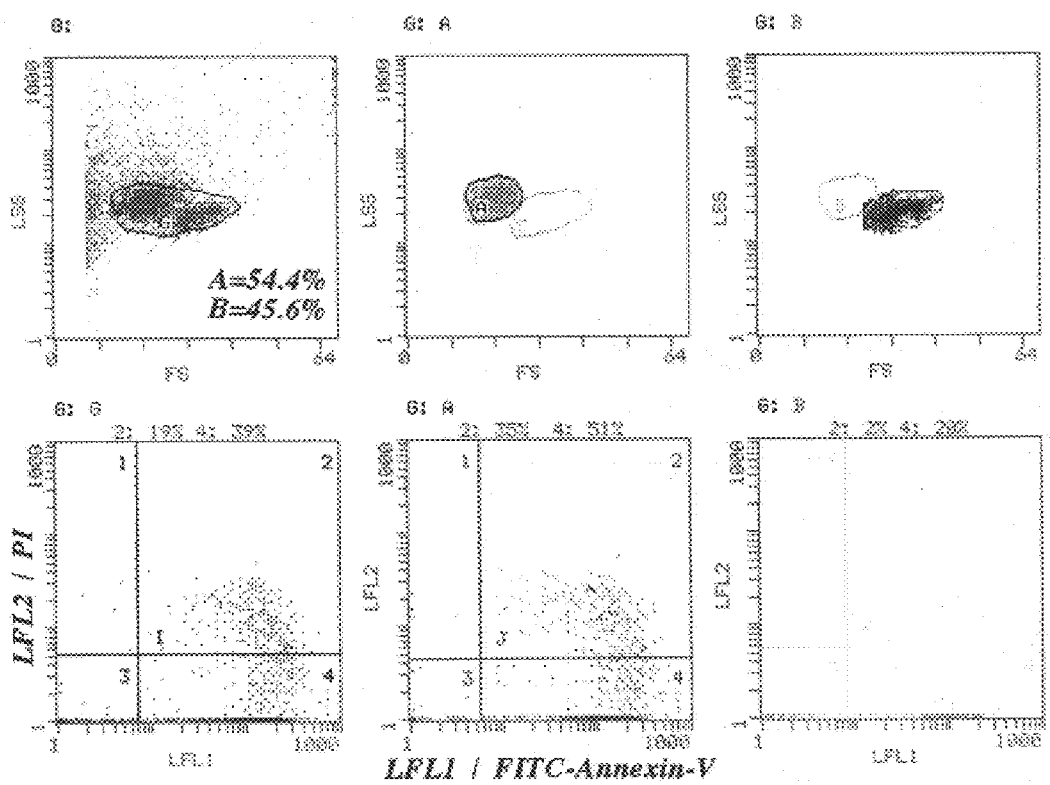
FIG. 1 is a diagram illustrating the change in side scatter versus the forward scatter of normal lymphocytes from human peripheral blood mononuclear cells (MNC) after staining with Annexin V-FITC and propidium iodide (PI) in large and small lymphocyte populations in the control and after ultrasonic energy treatment (FIG. 1). The lower right quadrant (4) represents the early apoptotic cells with Annexin V-FITC positive and PI negative binding. The upper right quadrant (2) contains the non-viable, late apoptotic or necrotic cells which are positive for Annexin V-FITC binding and for PI uptake. The lower left quadrant of each panel shows the viable cells with Annexin V-FITC and PI negative staining.
Figure 1B:
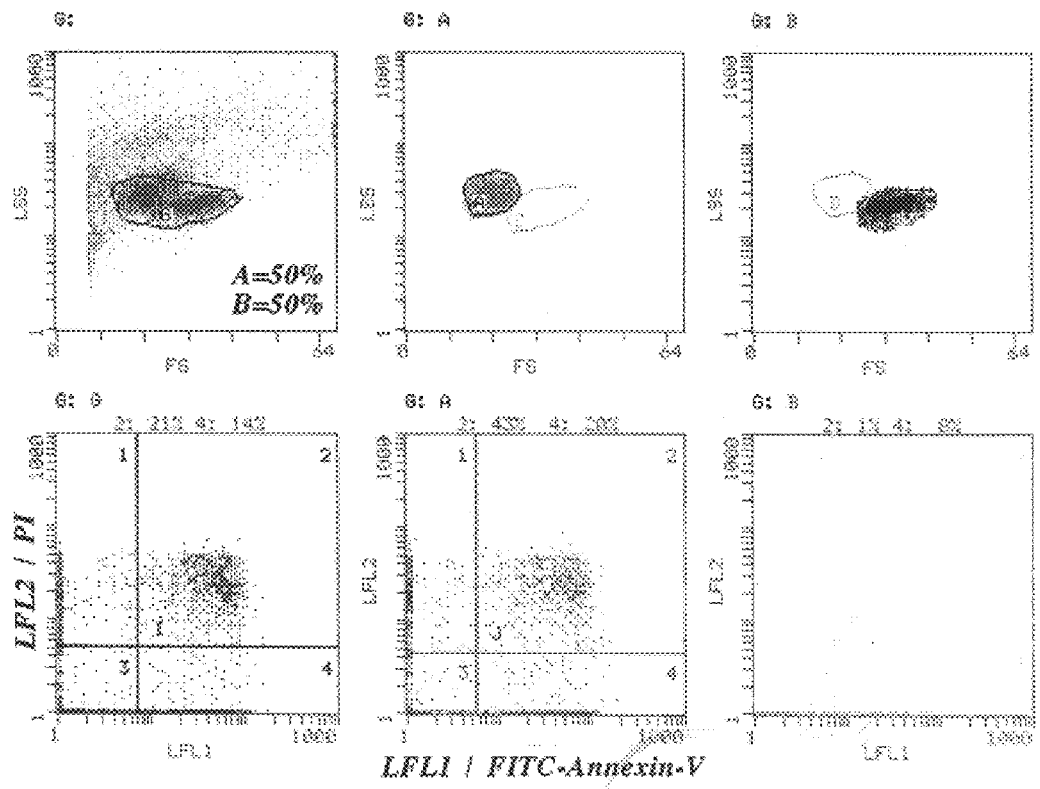

The present invention generally pertains to novel devices and methods for preventing and treating cancers and other proliferative disorders using ultrasonic energy effective for inducing apoptosis in the treated cells. The cancer prevention and therapy methods of the invention are fundamentally based upon a newly-discovered effect of ultrasonic energy on apoptosis of normal lymphocytes and cancerous cells. The present invention also provides a method for inducing apoptosis in aging cells and/or tissues that show functional deficit and to trigger renewal of cells and tissues.

4.1 Cancer Growth and Mechanism of Cell Death

Cancer is a disease of inappropriate tissue accumulation. This derangement is most evident clinically when tumor tissue bulk compromises the function of vital organs.

Chemotherapeutic cytotoxic agents are generally more effective in killing or damaging malignant cells than normal cells. However, the fact that they do harm normal cells indicates their potential for toxicity. Nearly all cytotoxic agents currently in use interfere with DNA synthesis, with the provision of precursors for DNA and RNA synthesis, or with mitosis. The mechanism of cell death after treatment with any single agent or combination of agents is complex and is likely to include more than one process. Such cytotoxic drugs can be most effective against cycling cells.

Because most clinically detectable tumors are composed mostly of noncycling cells, it is not surprising that chemotherapy is not always effective in eradicating cancer. The effectiveness of cytotoxic treatments has been limited by failure to deliver the cytotoxic agents to target cells in the core of some solid tumors. However, some chemotherapeutic agents interact with modulators of apoptosis such as Bcl-2 and activate apoptosis (Hannun, Y. A., 1997, J. Am. Soc. Hematol. 89:1845–1853). Some of the chemotherapeutic agents which have been shown to modulate apoptosis include Etoposide, VM26, mAMSA, Dexamethasone, Vincristine, cis-Platinum, Cyclophosphamide, Adriamycin, Paclitaxel, 5'-Flourouracil, 5'-Flouro-deoxyuridine, Camptothecin, Hydroxyurea, Ara-C, 5-Azacytidine, Nitrogen Mustard, Methotrexate, Chlorambucil, Bleomycin, BCNU, Actinomycin D or Melphalan.

Apoptosis is a general property of most cells, being fundamental for the organization and life span of any organism to control homeostasis and cell populations. It is necessary to achieve an adequate balance between the sufficient survival of cells and overwhelming proliferation and expansion. This is of particular importance to prevent malignant growth, but it is also necessary to limit expansion of immune cells challenged by pathogens or other stimuli, and as a defense mechanism to remove self-reactive lymphocytes (Steller, H. 1995, Science 267:1445–1449).

In aging cells and/or tissues that show functional deficit, apoptosis is a useful approach to increase the turnover of senescent cells and trigger the renewal of cellular function and structure.

From the perspective of cancer, apoptosis or programmed cell death, is both a mechanism which suppresses tumor development and as a predominant pathway in anticancer therapy. Examination of recognized classes of regulatory genes, for example, p53 or c-myc indicate that apoptosis might not require cell cycle progression but is signaled by transcriptional activation by both p53 (Attardi L. D. et al., 1996, EMBO J 15:3693–3701) and c-myc (Packham, G. et al., 1996, Oncogene13:461–469). Two major endogenous regulators of apoptosis have been identified, for example, the wild-type p53 protein which functions as an inducer of cell death especially in response to DNA damaging events (Lane, D. P., 1992, Nature 358:15), and reciprocally, the Bcl-2 oncogene which has an important antiapoptotic function (Yang, E. et al., 1995, Cell 80:285).

Apoptosis is an important cellular response to a variety of signals including ionizing radiation, UV radiation, heat, cytokines (TNF and IFNγ) as well as chemotherapeutic agents (Fisher, D. E., 1994, Genes Der. 8:2817–2830).

4.1.1. DNA Fragmentation

Apoptosis is a distinct morphological form of cell death which can be characterized by cell shrinkage, membrane disruption and chromatin condensation which finally leads to cell fragmentation. A striking characteristic of apoptosis is the formation of hyperchromatic nuclei containing DNA that is then redistributed to the nuclear margins. This marginalization correlates to the activation of $Ca^{2+}/Mg^{2+}$-dependent endonuceleases in the dying cell that digests the DNA into oligonucleosome-sized fragments that can be detected. Analysis of the fragments has shown that DNA fragmentation is a stepwise process, involving fragmentation at interrosette sites (generating DNA fragments larger than 300 kb), interloop sites (generating fragments of about 50 kb) and intranucleosomal sites (generating the characteristic 200 bp fragments) (Walker P. R., et al., 1994, Biochem. Cell Biol. 72:615–623).

It has been observed that ultrasonic energy or therapeutic ultrasound (ULS) induces apoptosis in normal and leukemic human lymphocytes as revealed by flow cytometry. See Section 6, infra.

4.2 Apoptosis and Antioxidants

Cellular antioxidant defense mechanisms such as the reactive-oxygen scavenger enzymes superoxide dismutase and catalase can control apoptosis (Buttke, M. T. and Sandstrom, P. A., 1994, Immunol. Today 15:7–10). For example, there is evidence that the proto-oncogene Bcl-2 suppresses apoptosis through the regulation of an antioxidant pathway (Hockenberg, D. M. et al., 1993, Cell 75:241–251). However, other experimental data supports the concept that Bcl-2 inhibits apoptosis by altering Ca fluxes. Moreover, the antioxidant N-acetyl-cysteine induced apoptosis in vascular smooth muscle cells (U.S. Pat. No. 5,571,523, issued Nov. 5, 1996 to M-E Lee et al). Thus, the present invention also includes a method for inducing apoptosis in vascular muscle cells, precancerous and cancerous cells using a combination of ultrasonic energy and antioxidant therapy. The methods of the present invention are directed to inhibit Bcl-2 induced antiapoptotic activity that gives survival advantage to cancer and other cell types that overexpress the Bcl-2 protein product. Suitable antioxidants include, but are not limited to, one or more of N-acetylcysteine, vitamin E, glutathione, vitamin C, cysteine, methionine or 2-mercaptoethanol.

The antioxidant formulations or pharmaceutical compositions may be administered intravenously, intraperitoneally, subcutaneously, intramuscularly, intrathecally, orally, rectally, topically or by aerosol. Formulations may be administered in a variety of forms including for example, solid (tablets, pills, powders), semi-solid and liquid dosage forms, suspensions, liposomes, injectable and infusible solutions. The formulations may be in unit doses or multi-doses sealed containers. The methods of this invention may be used in combination with other therapies to treat cancer, arteriosclerosis, vascular and fibrotic proliferative diseases, retinopathies, eczema or psoriasis.

Patient dosages for oral administration would vary according to the oxidant used, for example, the adult dose for vitamin E would range from 200 I.U. to 1000 I.U per day.

4.3. Growth Factors

Overexpression of growth factors leads to suppression of cell death and has significant implications in the treatment of cancer. For example, the growth and proliferation of epithelial cells in prostate cancer is influenced by EGF, TGF-alpha, TGF-beta, NGF and FGF. The overexpression of these growth factors prevents DNA fragmentation and apoptotic mechanism (Chung, L. W. et al., 1992, J. Cell Biochem. Supplm. 16H:99–105). The methods of the present invention can induce apoptosis of growth factor receptor-bearing precancerous and cancerous cells and supporting stromal cells with ultrasonic energy.

4.4 Target Cancers

Cancers that can be prevented and/or treated by the ultrasound therapeutic methods of the present invention include, but are not limited to, human sarcomas and carcinomas, e.g., colon carcinoma, pancreatic cancer, breast cancer, ovarian cancer, prostate cancer, fibrosarcoma, myxosarcoma, liposarcoma, chondrosarcoma, osteogenic sarcoma, chondroma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. Specific examples of such cancers are described in the sections below.

The possible mechanisms of action of ultrasonic energy or ultrasound therapy presented above are in no way meant to limit the scope of the invention and are presented purely for explanatory and/or illustrative purposes.

4.4.1. Prostate Cancer

The invention is illustrated, by way of protocols for ultrasound therapy alone or in combination with conventional therapies, for example, surgical removal of the primary cancer, radiation therapy, hormonal therapy or chemotherapy in treatment of prostate cancer.

In making decisions about treatment for prostate cancer, clinicians consider the patient's age and general health, the clinical state and histological grade of the cancer, and factors concerning quality of life. Cytoxtoxic chemotherapy is largely ineffective in treating prostate cancer. Accordingly, there is a great demand for improved prostate cancer treatments.

The present invention provides a method of preventing and treating prostate cancer comprising ultrasound therapy alone or in combination with a conventional therapy, for example, radiation therapy, hormonal therapy or chemotherapy to induce apoptosis and inhibition of the growth of the tumors in patients. When a conventional therapy is administered along with ultrasound therapy, it is administered according to protocols and dosage ranges known to those skilled in the art. The therapeutic regimen is applied either preoperatively, i.e., to the tumor in situ or postoperatively, in the region of the tumor after removal of the primary cancerous lesion.

An especially important aspect of the methods of the invention is in the prevention and treatment of cancer and other proliferative diseases by launching the apoptotic machinery of the cell. The therapeutic use of ultrasonic energy for inducing apoptosis has not been used or proposed heretofore. The following non-limiting examples illustrate certain therapeutic methods in accordance with the invention.

4.5 Ultrasonic Treatment

4.5.1 Invasive Ultrasonic Treatment

Figure 4:
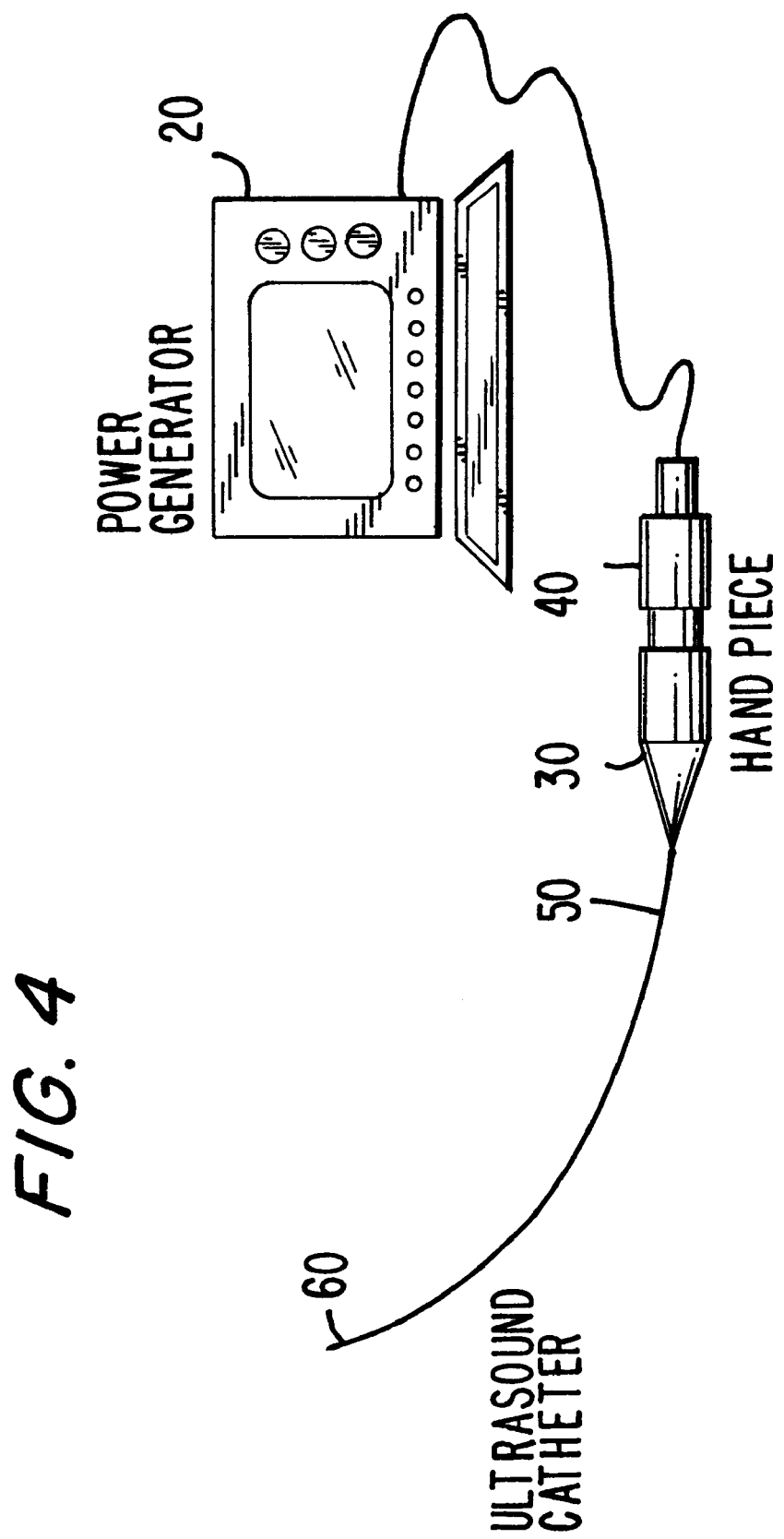
FIG. 4 is a schematic illustration of an invasive ultrasonic device in accordance with one embodiment of the system.

An invasive ultrasonic device can include the following elements shown in the embodiment of FIG. 4. A power generator 20, supplies an apoptosis inducing system with sufficient electrical energy needed to produce ultrasonic energy. An ultrasound transducer 30 in a handpiece 40, includes piezoelectric elements (not shown) that convert electrical energy into ultrasonic energy. An ultrasonic transmission wire 50 is connected at its proximal end to the transducer and has an ultrasound tip 60 at the other end. The ultrasonic energy can be transmitted as a longitudinal vibration of transmission wire 50 which thereby directs ultrasound energy into the arterial system of a patient (not shown).

The frequency level of ultrasound energy used is in the range of 1 kHz to 3 kHz, typically 2 kHz in vitro, in vivo and in human precancerous, cancerous and target cell studies, and 15 kHz to 250 kHz, typically 45 kHz in in situ cancer studies.

Power is supplied by power generator 20. Tumor cell irradiation is performed with a power, or example, of about 20. Tumor cell are irradiated with a power, for example of about 20±2 W in vivo, and of about 12.0±0.9 W in humans. System power is translated into longitudinal displacement of ultrasound tip 60, measuring 150±25 $\mu$m initial studies and 10–15 $\mu$m in cellular application.

The exact operating parameters will be determined depending on the specific ultrasound system being used as well as on the target tissue.

4.5.2 Noninvasive Ultrasonic Treatment

Non-invasive ultrasound technology enables delivery of ultrasonic energy from a source outside the human body to a specific external location such as leukemic blood cells undergoing leukophoresis, or to an internal location in the body. The intensity level of the energy of the treatment should be high enough to create acoustic transient cavitation at the locus of therapy.

In order to eliminate any risk in that respect, the energy is preferably transmitted to the treatment area in such a way that the energy is focused only at the target location. Being unfocused along the way, minimal heat is created and little risk is involved. Either continuous wave or pulsed wave ULS can be used. The intensity of the ultrasound energy treatment should be high enough to accelerate the delivery of a chemotherapeutic agent into the core of a target tissue such as a soild tumor.

The device can be made compatible with ultrasound imaging systems by the addition of a dedicated therapeutic ultrasound probe. The combined system can serve as both an imaging probe and a treatment probe, thereby transmitting the required treatment energy to the selected target under ultrasound imaging. A software package can add the capability to support the visualization of the target, and the activation of the therapeutic energy transmission at the target.

The operation and handling of the device will also be similar to ultrasound imaging systems, with the addition of activation of non-invasive therapeutic ultrasound transmission.

A system for the prevention and/or treatment of cancer or cell proliferative diseases in accordance with the present invention may typically include a therapeutic ultrasound probe, preferably containing therapeutic and imaging capabilities. The therapeutic ultrasound element can be based on any method for focusing ultrasound (e.g., geometric, annular array, phase array). The system will typically also include a control unit for controlling the ultrasonic energy output, which may preferably include a monitor, similar to regular imaging monitors, and more preferably, along with the software and hardware, suitable for operating the combined imaging and therapeutic transducer.

4.6 EXAMPLE

Application of Ultrasound therapy in Normal and Leukemic Lymnphocytes and in Experimental Leukemia The effect of therapeutic ultrasound on induction of apoptosis was studied in normal and leukemic human lymphocytes, and in HL-60, an acute promyelocytic human leukemic cell line. Peripheral blood mononuclear cells were obtained from healthy adult donors and patients suffering from chronic lymphatic leukemia (CLL).

The blood mononuclear cells (MNC) were isolated by density gradient centrifugation on Ficoll-Paque gradient (D=1.077). The MNC layer was collected from the Ficoll-Paque plasma interphase, washed, pelleted with phosphate buffered serum (PBS) and dispersed in RPMI-1640 containing 10% fetal calf serum (FCS). The MNC were activated with 125 $\mu$g/mL phytohemaglutinin (PHA) by culturing the cells in RPMI- 1640 medium with 10% FCS at 37° C. in a humidified atmosphere containing 10% $CO_2$ for different time intervals (48 hours and 72 hours). The PHA sensitized cells were washed twice with RPMI-1640 medium and resuspended at appropriate concentrations.

The blood MNC and the HL-60 leukemic cells were treated with ultrasonic energy as follows:

$2.5 \times 10^6$ per 5 mL RPMI-1640 with 10% FCS were suspended in 16×125 mm culture tubes (Corning-Staffordshire, UK). The MNC were then exposed to ultrasonic energy using a sonicator which consists of a resonant length (90 mm) of a vertically suspended thin titanium probe (diameter 2 mm) and which resonates at a frequency of 20 kHz and variable power levels. To prevent aerosol formation during sonication, the depth of immersion of the probe was adjusted so that the meniscus of the liquid was in contact with the ultrasonic transmission member wire of the probe at a displacement node.

In addition, the effect of ultrasonic treatment on the temperature of a suspension of HL-60 leukemic promyelocytic cells was studied by using 0.5, 1.0, 1.5 and 3.0 watts for periods of 5, 15 or 30 seconds. The temperature was measured using a thermocoupler which was placed in the test tube.

The viability of the blood MNC and the HL-60 cells subjected to ultrasonic energy was tested by the trypan blue exclusion method. Aliquots of MNC were removed and the dye (0.4% in phosphate buffer saline, PBS) was added to the cell suspension. The extend of dye uptake is indicative of cell damage. The viable cells were counted using a hemocytometer. Each experiment was performed with a given number of viable cells after sonication. Controls consisted of the same number of unsonicated cells.

The LD50 of the therapeutic ultrasound was found to be 1.5 watts for 15 sec for blood MNC and 1.5 watts for 10 sec or 0.5 watts for 30 sec for HL-60 cells at a frequency of 20 kHz. This dosage was used in all experiments and can be considered a minimal effective dosage.

The results of varying levels of ultrasonic energy on temperature of HL-60 cell suspensions are shown in Table 1. Within the power (0.5 to 3.0 watts) and time intervals (5, 15, 30 sec) used, there was no significant change in the temperature of the HL-60 cell suspensions as measured by the thermocouple. These results indicate the safety of ultrasound therapy in biological cell systems.

The effect of ultrasound therapy on apoptosis was analyzed by flow cytometry to monitor the change in light-scattering properties of the blood MNC and HL-60 cells as a consequence of apoptosis.

The plasma membrane integrity was analyzed by an assay for detection of early apoptotic cells using fluorescein labeled Annexin V and propidium iodide as described by Vermes (Vermes, I., 1995, J. Immunol. Methods 184:34–51) and Fadok (Fadok, V. A., 1992, J. Immunol. 143:2207). One of the alterations in the plasma membrane is the translocation of phosphotidylserine (PS) from the inner site of the plasma membrane to the outer layer at the external surface of the cell. Annexin V, which has a high affinity for PS, acts as a sensitive probe for PS exposed upon the cell membrane and gives a measure of the early phase of apoptosis.

Figures 1, 2A:
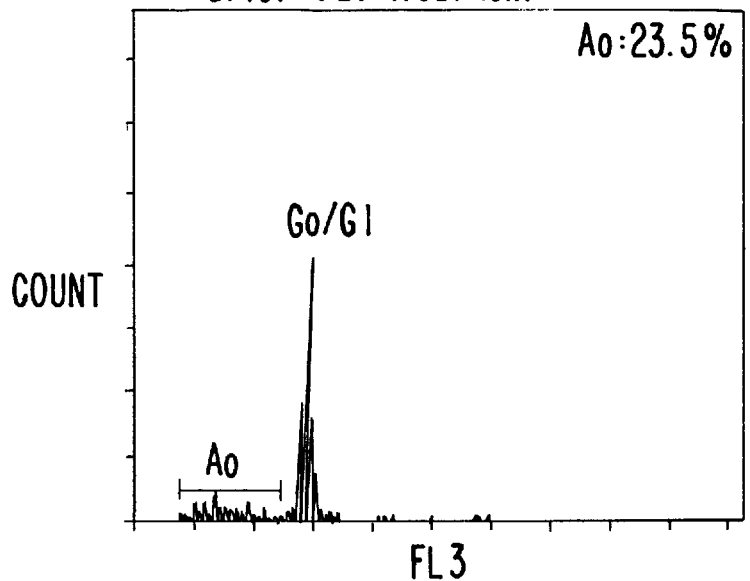
FIGS. 2a, 2b, 2c and 2d are scattergrams representing the apoptotic cells as the sub-Go peak (Ao) in the control or ultrasonic energy treated PHA-activated lymphocytes (after 72 hours), lymphocytes taken from a chronic lymphocytic leukemia (CLL) patient (after 48 hours), lymphocytes from a patient suffering from CLL (after 8 hours) and HL-60 promyelocytic leukemic cells (after 90 min) respectively.
Figures 2, 2A:
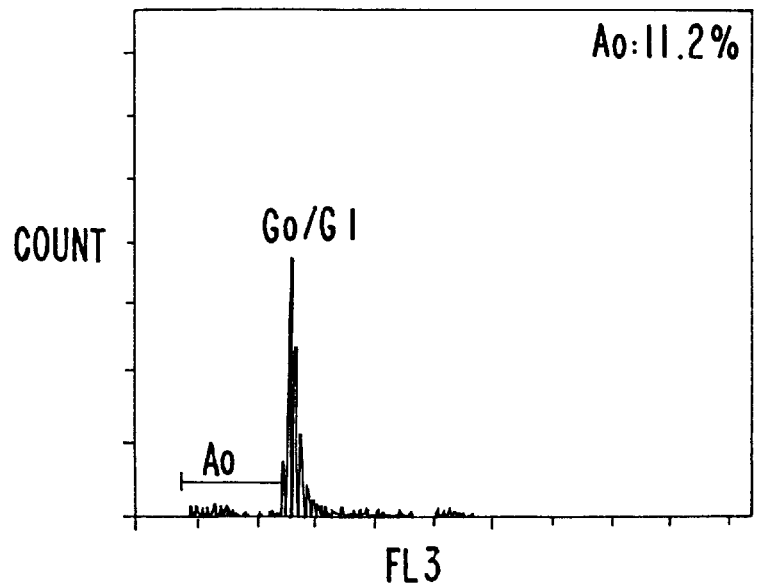

There was clear evidence of apoptosis in ultrasound treated normal lymphocytes after 48 hours. The percentage of total blood MNC in early apoptosis after ultrasound treatment was 39% (Annexin $V^+/PI^-$) in comparison with the control untreated blood MNC showing 14% of cells in early apoptosis (FIG. 1). The percentages of small and large blood MNC populations (FIG. 1 gate G:A and gate G:B respectively) in early apoptotic state were higher (51% and 20%, respectively) than those in the untreated control cells (20% and 8%, respectively). However, there was no significant difference between the ultrasound treated and untreated cells twenty-four hours after ultrasound treatment.

The second method employed to detect apoptotic cells was by measuring the presence of sub-Go peak (Ao) in the cellular DNA profile following staining with the DNA specific fluorochrome propium iodide according to routine procedures published in the literature (Vermes, I., 1995, J. Immunol. Methods 184:34–51; Fadok, V. A., 1992, J. Immunol. 148:2207; McCloskey, T. W. et al., 1994, Clin. Immunol. Immunopathol. 71:14–18; and Nicoletti, I. Et al., 1991, J. Immunol. 139:271). Apoptotic cells showed the presence of cellular DNA profile below the $G_0/G_1$ peak, following staining with propidium iodide.

Figures 1, 2B:
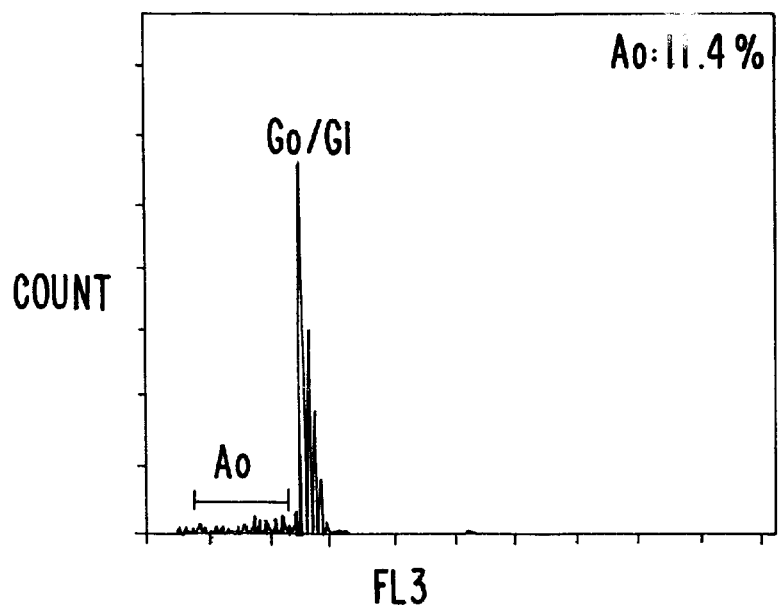
Figures 2, 2B:
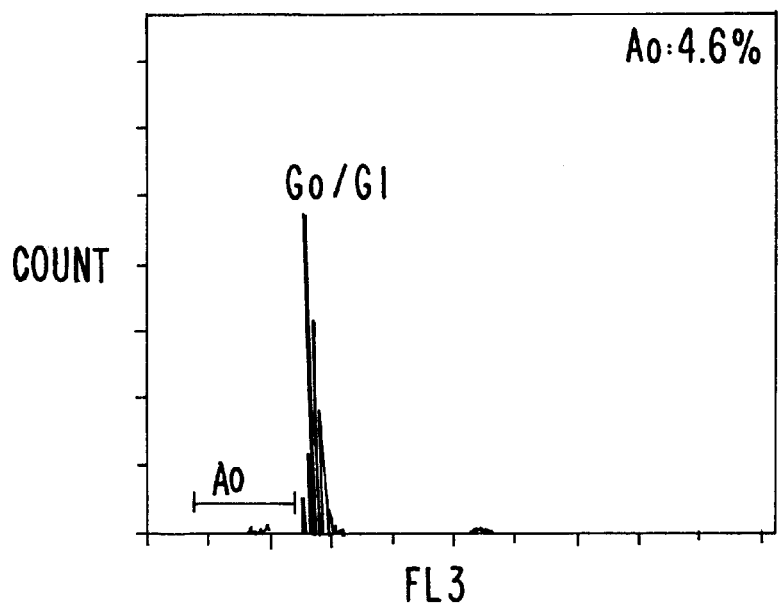
Figures 1, 2C:
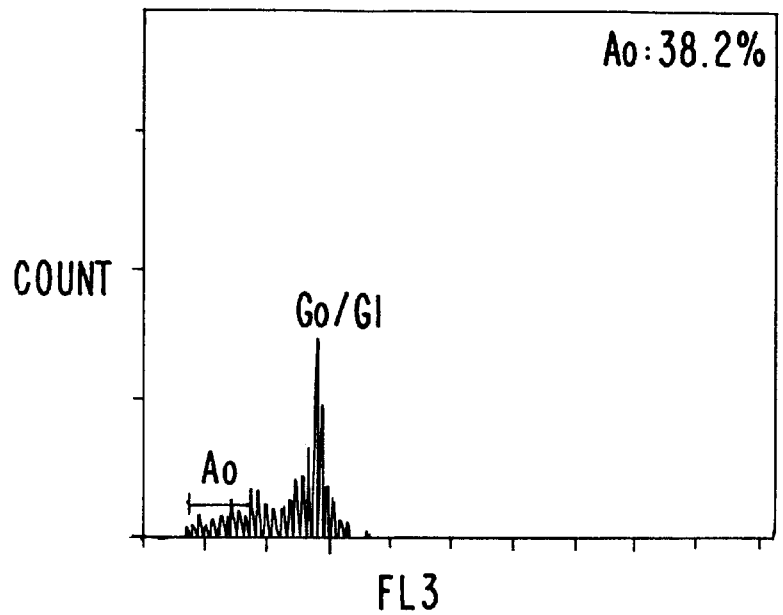
Figures 2, 2C:
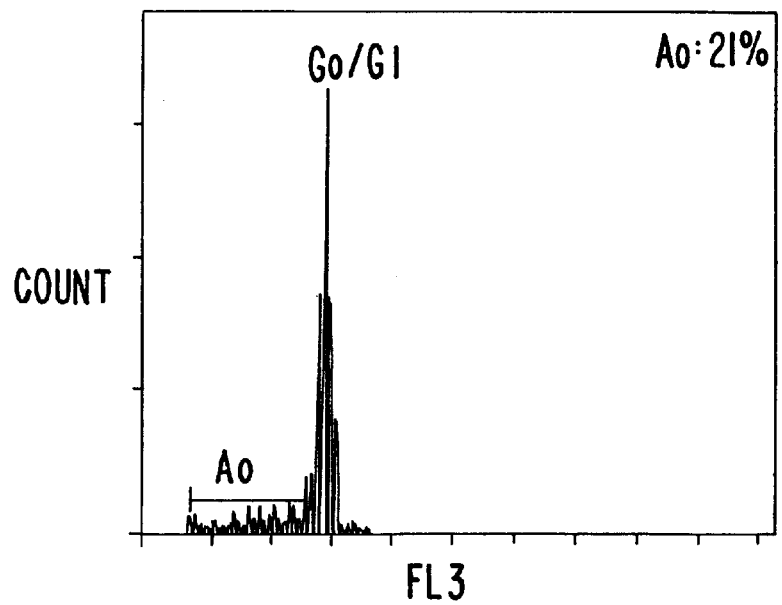
Figures 1, 2D:
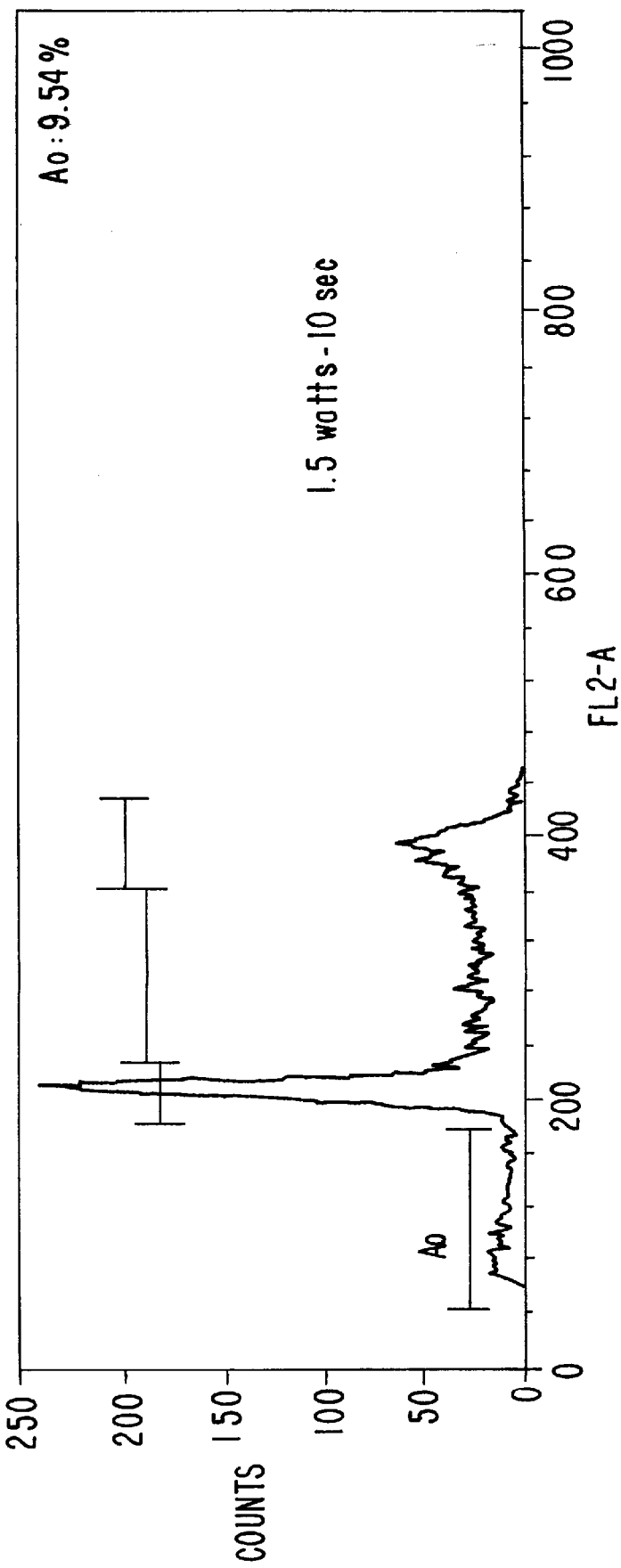

The hypo-diploid cell population ($A_0$ cells) indicative of degraded DNA in apoptotic cells, was 2.1 times higher in PHA-activated normal blood MNC than the control untreated cells following 72 hours of culture (FIG. 2a). Blood MNC from CLL patients showed a sub-$G_0$ peak 48 and 8 hours after ultrasound treatment with an increased number of apoptotic cells in comparison to the control (FIGS. 2b and 2c). HL-60 leukemic cells showed a sub $G_0$ peak 90 min after ultrasound treatment with a 3.2 fold higher peak than in the control (FIG. 2d).

TABLE 1

Effect of Ultrasound Therapy on Temperature (° C.) of HL-60 Cell Suspension

| Ultrasonic Energy Watt/Time (sec) | Temperature before ULS Therapy | Temperature during ULS Therapy | | Temperature 5 sec. after ULS Therapy |
|---|---|---|---|---|
| 0.5/5 | 23.3 | 23.3 | 23.3 | 23.3 |
| 0.5/15 | 23.5 | 23.8 | 24 | 24 |
| 0.5/30 | 25 | 25.5 | 25.8 | 25.8 |
| 1/5 | 23 | 23.2 | 23.2 | 23.2 |
| 1/15 | 23.5 | 24 | 24.8 | 24.8 |
| 1/30 | 24.5 | 25 | 26 | 26 |
| 1.5/5 | 23 | 23.2 | 23.5 | 23.5 |
| 1.5/10 | 23.5 | 24 | 24.3 | 24.3 |
| 1.5/15 | 24 | 24.5 | 25 | 25 |
| 1.5/30 | 24.5 | 25.5 | 26.5 | 26.5 |
| 3/5 | 23 | 23 | 23.5 | 23.5 |
| 3/15 | 23.5 | 24.5 | 25 | 25 |
| 3/30 | 24.5 | 26 | 27.7 | 27.6 |

The third method used to study apoptosis was to monitor morphological changes in the cells after staining with May Grünwald-Giemsa. Morphological changes during apoptosis include condensation of nuclear chromatin which often takes on a concave shape, and DNA in condensed (picnotic) chromatin which exhibits hyper chromasia staining strongly with light absorbing dyes.

Figure 3A:
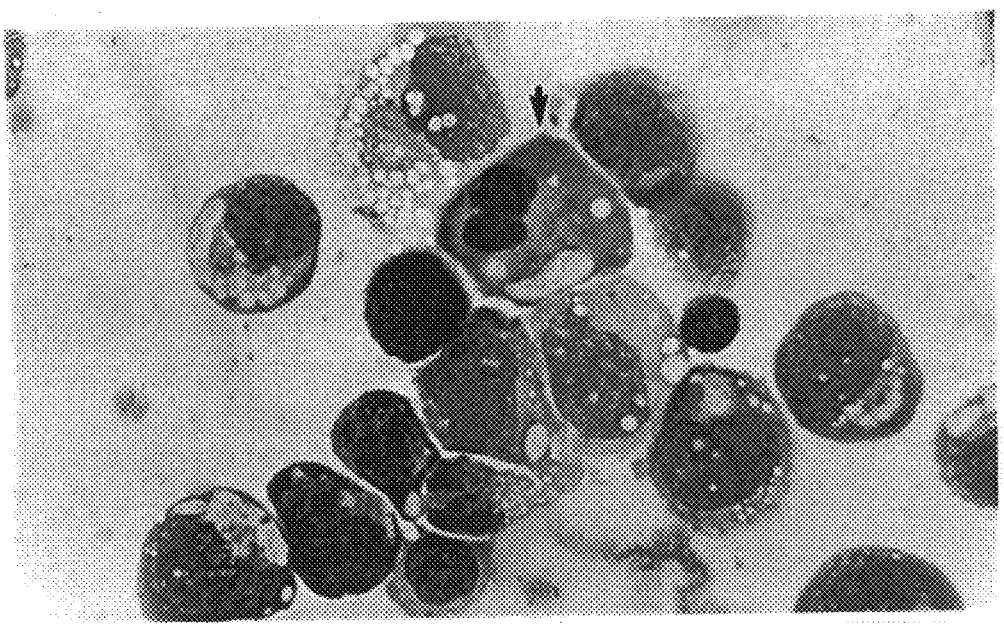
FIGS. 3a, 3b and 3c are photographs of cells showing the morphology of PHA-activated MNC, and lymphocytes from a patient suffering from CLL after 72 hours and after 48 hours, respectively, after ultrasonic treatment. Nuclear Chromatin is demonstrated by use of May Grunwald-Giemsa Staining.
Figure 3B:
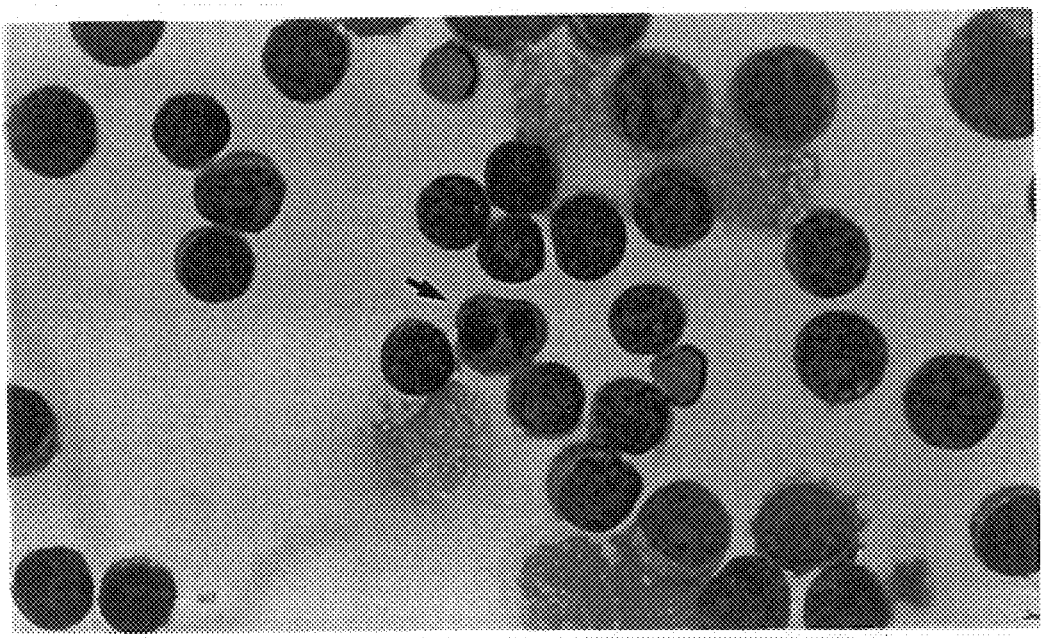
Figure 3C:
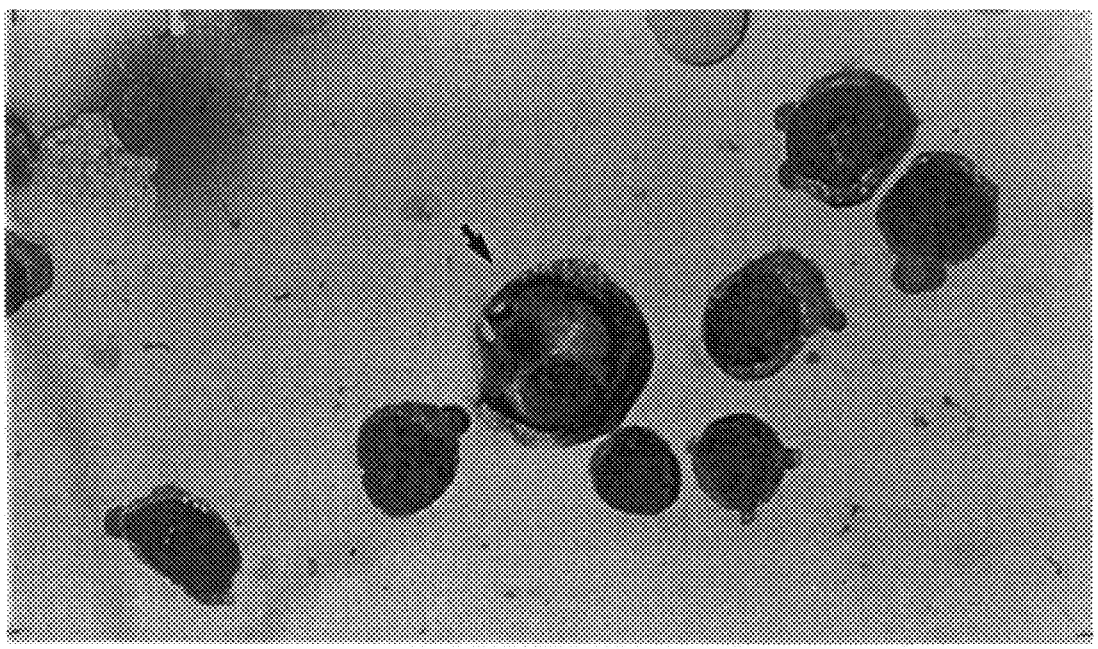

FIGS. 3a, 3b and 3c indicate the morphological changes of MNC undergoing apoptosis, including the condensation of nuclear chromatin and nuclear fragmentation (shown by arrows) in PHA-activated ultrasound treated normal MNC after 72 hours of culture (FIG. 3a), and in ultrasound treated CLL MNC (FIG. 3b) after 48 hours in culture as well as phagocytized apoptotic cells (FIG. 3c).

Thus therapeutic ultrasonic energy induced early apoptosis in normal blood mononuclear cells 48 hours after ultrasound treatment (as indicated by Annexin $V^+/PI^-$ cells) and late apoptosis (as indicated by Annexin $V^+/PI^+$ cells). At 72 hours after ultrasound treatment, PHA-activated MNC cells and CLL MNC cells contain degraded DNA and show a morphology that is characteristic of apoptosis. These data indicate the unexpected benefit that ultrasound therapy in accordance with the present invention is effective in inducing apoptosis or programmed cell death in precancerous, cancerous and target cells.

The present invention is not to be limited in scope by the embodiments disclosed in the examples which are intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Various publications are cited herein, the disclosures of which are incorporated by reference in their entireties.

It will thus be seen that the objects set forth above, among those made apparent from the preceding description, are efficiently attained and, since certain changes may be made in carrying out the above method and in the constructions set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall there between.

What is claimed is:

1. A method of preventing development of cancer in an individual having a region of aging or precancerous cells, the method comprising applying in the region of aging or precancerous cells an effective amount of ultrasonic energy of sufficient dosage to induce apoptosis of the aging or precancerous cells.

2. The method according to claim 1, wherein the dosage of ultrasonic energy supplied is above at least 22.5 watt/sec and the cavitation threshold of blood.

3. The method according to claim 1, wherein the ultrasonic energy supplied has a frequency in the range of about 1 kHz to about 3 MHz.

4. The method according to claim 1, wherein the ultrasonic energy supplied has a frequency in the range of about 15 kHz to about 250 kHz.

5. The method of claim 1, wherein ultrasonic energy is applied with an ultrasonic energy source for providing ultrasonic energy, a transmitter for transmitting the ultrasonic energy to the region of the aging or precancerous cells, and a control unit controlling the ultrasonic energy source, the ultrasonic energy source, the transmitter and the control unit being constructed and arranged to transmit the ultrasonic energy to the aging or precancerous cells in an amount sufficient to induce apoptosis of the aging or precancerous cells present in the region.

6. A method of treating cancer in an individual, comprising applying to an individual having cancer cells in a region of the body, ultrasonic energy in the region of the cancer with an effective amount of ultrasonic energy to induce apoptosis of the cancer cells.

7. The method according to claim 6, wherein the ultrasonic energy supplied is above at least 22.5 watt/sec and the cavitation threshold of blood.

8. The method according to claim 6, wherein the ultrasonic energy supplied has a frequency in the range of about 1 kHz to about 3 MHz.

9. The method according to claim 6, wherein the ultrasonic energy supplied has a frequency in the range of about 15 kHz to about 250 kHz.

10. The method according to claim 6, wherein applying ultrasound in the region of the cancer occurs after surgical removal of the cancer.

11. The method according to claim 6, comprising administration of an antioxidant.

12. The method according to claim 6, comprising administration of an effective amount of at least one antioxidant selected from the group consisting of vitamin E, N-acetylcysteine, glutathione, vitamin C, cysteine, methionine, 2-mercaptoethanol and photosensitizing molecules.

13. The method according to claim 6, comprising administration of an effective amount of hormonal therapy.

14. The method according to claim 6, comprising administration of an effective amount of radiation therapy.

15. The method according to claim 6, comprising administration of an effective amount of at least one chemotherapeutic agent.

16. The method according to claim 15, comprising administration of an effective amount of ultrasonic energy to accelerate the delivery of the chemotherapeutic agent to a target.

17. The method of claim 6, wherein ultrasonic energy is applied with an ultrasonic energy source for providing ultrasonic energy, a transmitter for transmitting the ultrasonic energy to the region of the cancer cells, and a control unit controlling the ultrasonic energy source, the ultrasonic energy source, the transmitter and the control unit being constructed and arranged to transmit the ultrasonic energy to the cancer cells in an amount sufficient to induce apoptosis of the cancer cells present in the region.

18. A method of treating arteriosclerosis in an individual having arteriosclerosis, comprising applying ultrasonic energy to smooth muscle cells in the region of an atheromatous plaque in the vessel wall with an effective amount of ultrasonic energy to induce apoptosis of the smooth muscle cells.

19. A method according to claim 18, comprising administration of an antioxidant.

20. The method according to claim 18, comprising administration of at least one antioxidant selected from the group consisting of vitamin E, N-acetylcysteine, glutathione, vitamin C, cysteine, methionine, 2 mercaptoethanol and photosensitizing molecules.

21. A method of preventing or treating cell proliferative diseases comprising applying ultrasonic energy in the region of proliferating cells with an effective amount of ultrasonic energy to induce apoptosis of the proliferating cells.

22. The method according to claim 21, wherein the cell proliferative diseases are selected from the group consisting of eczema, psoriasis, retinopathies, vascular diseases and fibrotic diseases.

23. A method of inducing apoptosis in a cell expressing a growth factor receptor, the method comprising applying ultrasonic energy with an effective amount to induce apoptosis in the cell.

24. A method according to claim 23, wherein the growth factor receptor is selected from the group consisting of EGF, TGF, NGF, FGF, IGF or PDGF.

* * * * *